(12) United States Patent
Chemat et al.

(10) Patent No.: US 8,802,021 B2
(45) Date of Patent: Aug. 12, 2014

(54) MICROWAVE INTEGRATED SOXHLET

(75) Inventors: Farid Chemat, Avignon (FR); Valerie Tomao, Avignon (FR); Francesco Visinoni, Sorisole (IT)

(73) Assignees: Milestone S.r.l., Soriole (BG) (IT); Universite d'Avignon et des Pays de Vaucluse, Avignon (FR)

( * ) Notice: Subject to any disclaimer, the term of this patent is extended or adjusted under 35 U.S.C. 154(b) by 1177 days.

(21) Appl. No.: 12/523,846

(22) PCT Filed: Jan. 21, 2008

(86) PCT No.: PCT/EP2008/000421
§ 371 (c)(1),
(2), (4) Date: Sep. 10, 2009

(87) PCT Pub. No.: WO2008/089937
PCT Pub. Date: Jul. 31, 2008

(65) Prior Publication Data
US 2010/0022788 A1    Jan. 28, 2010

(30) Foreign Application Priority Data
Jan. 22, 2007  (EP) ..................................... 07100931

(51) Int. Cl.
*B01D 11/00* (2006.01)
*H05B 6/64* (2006.01)
*B01D 5/00* (2006.01)
*G01N 1/44* (2006.01)
*B01D 11/02* (2006.01)

(52) U.S. Cl.
CPC ............ *B01D 5/0057* (2013.01); *B01D 5/0063* (2013.01); *G01N 1/44* (2013.01); *B01D 11/0211* (2013.01)

USPC ........... 422/261; 422/269; 422/280; 422/281; 422/614; 219/679

(58) Field of Classification Search
None
See application file for complete search history.

(56) References Cited

U.S. PATENT DOCUMENTS

| 3,397,115 A | 8/1968 | Tobey |
| 5,002,784 A * | 3/1991 | Pare et al. ..................... 426/241 |
| 5,447,077 A | 9/1995 | Lautenschlager |
| 5,711,857 A | 1/1998 | Armstrong |
| 5,750,008 A * | 5/1998 | Lautenschlager ............... 203/43 |
| 5,843,311 A | 12/1998 | Richter et al. |
| 6,242,723 B1 * | 6/2001 | Lautenschlager ............. 219/679 |
| 2005/0082157 A1 | 4/2005 | Kiran Babu et al. |

FOREIGN PATENT DOCUMENTS

| WO | WO-9744109 A1 | 11/1997 |
| WO | WO-2004062766 A1 | 7/2004 |

OTHER PUBLICATIONS

Wo 9744109, DiMartino, J., A device and instillation for microwave extracting of organic compounds from a sample, 1997, pp. 1-12, (English translation).*
ES 2212748, Luque de Castro, et al., Device for the microwave accelerted extraction of components of solid samples and applications thereof, 2005, pp. 1-11, (English translation of WO 2004062766).*

(Continued)

*Primary Examiner* — Yate K Cutliff
(74) *Attorney, Agent, or Firm* — Marshall, Gerstein & Borun LLP

(57) ABSTRACT

The present invention relates to a new method of extraction of solid compounds by microwaves and to the apparatus used in said method.

25 Claims, 4 Drawing Sheets

(56) References Cited

OTHER PUBLICATIONS

Figure 1:
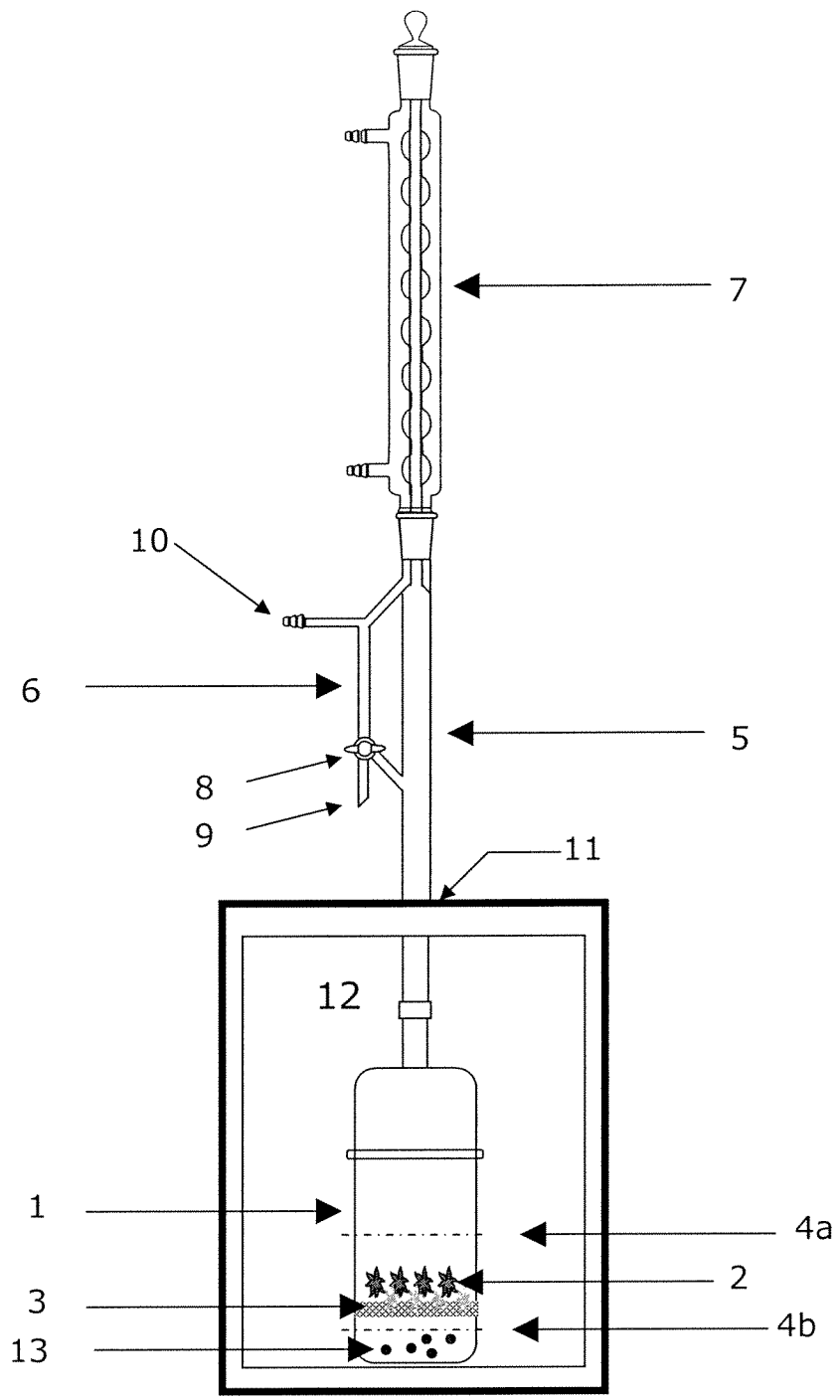

Budzinski et al., "Focused Microwave Assisted Extraction of Polycyclic Aromatic Compounds from Standard Reference Materials, Sediments and Biological Tissues," *Polycyclic Aromatic Compounds*, 9:225:232 (1996).

Lopez-Avila et al., "Microwave-Assisted Extraction as an Alternative to Soxhlet, Sonication, and Supercritical Fluid Extraction," *J. AOAC Int.*, 79:142-156 (1996).

McMillin et al., "Abbreviated microwave extraction of pesticides and PCBs in soil," *Spectroscopy*, 13:41-50 (1996/1997).

International Search Report and Written Opinion for PCT/EP2008/000421 dated Jun. 4, 2008.

International Search Report and Written Opinion for PCT/EP2008/000421 dated Jul. 9, 2008.

\* cited by examiner

MICROWAVE INTEGRATED SOXHLET

FIELD OF THE INVENTION

The present invention relates to a method for the extraction of compounds from solid material, in particular organic compounds, and to an apparatus for carrying out said method. In particular, the method is concerned with extraction by microwaves based on the Soxhlet method.

BACKGROUND OF THE INVENTION

Extraction of solid material is traditionally performed by standard techniques such as a Soxhlet extraction. The Soxhlet method proceeds by iterative percolation of the sample to be extracted with recondensed vapours of solvent. This method is one of the most used technique for extraction of organic contaminants for example. Since this process can be quite lengthy, new methods using microwave radiation have been developed.

For example, WO 2004/062766 A1 describes a microwave-accelerated extraction of components of solid samples. The method consists in heating up the solvent by conventional electrical heating, allowing the solvent to reflux over a glass tube containing the sample to be extracted. The sample to be extracted is at the same time subjected to microwaves. This allows the extraction of compounds which are only weakly polar or apolar such as polycyclic aromatic hydrocarbons (PAHs), polychlorinated biphenyls (PCBs), dioxins, etc.

Another method for extracting organic compounds from a solid sample by microwaves is described in WO 97/44109 and consists in subjecting a sample in a solvent to microwave radiation such that the solvent can reflux and such that the organic compound can be extracted in a way similar to a Soxhlet extraction. In the method, the solid material is placed in a movable, porous container, which can be retracted out of the solvent.

Using a microwave assisted extraction process such as those described above presents the advantage that the whole extraction process is accelerated. However, it has been found that the moisture content of samples to be extracted is a defining parameter for the recovery yield, when carrying the methods of the prior art. For instance, Lopez Avila et al. (*J. AOAC Int.* 1996, 799, 1, 142-156) and McMillin et al. (*Spectrosc.* 1997, 13, 41-50) have reported that the recovery of polar pollutants is improved with moisture. Furthermore, Budzinski, H. et al. in *Polycyclic Aromatic Compounds* 1996, 9, 225-232 have reported that the maximum recovery for PAHs is obtained when the moisture content of the sample is between 20 to 100%, preferably about 30%. When using dried samples, the recovery yield drops dramatically to about 15%.

The prior art methods are therefore limited in terms of solvents choice, nature of the solid material to be extracted, moisture content etc.

OBJECT OF THE INVENTION

In view of the above, there is thus a need to provide an improved microwave assisted extraction process which overcomes at least some limitations of the known processes.

SUMMARY OF THE INVENTION

Accordingly, the invention provides a device suitable for the extraction of solid material by microwave irradiation, and a method for the extraction of solid material.

Thus, the invention relates, in a first aspect, to a device suitable for the extraction of solid material by microwave irradiation, said device comprising
 a. A microwave oven,
 b. A base vessel placed in the microwave oven, said base vessel containing a polytetrafluoroethylene/graphite compound in the form of a stir bar and/or particles and an inner support for placing the solid material to be extracted, said inner support being placed at a defined distance above the bottom of said vessel,
 c. An extraction tube placed on top of the base vessel comprises a side arm provided with at least one valve and at least one opening, the microwave oven being provided with an opening on its upper surface such that the extraction tube extends from inside the microwave oven to outside.

In a second aspect, the invention proposes a method for the extraction of solid material, the method comprising the steps of:
 a. Placing the solid material to be extracted and a solvent in a base vessel, said solid material being placed on a support placed at a defined distance above the bottom of said vessel,
 said solvent being, when starting the method, in a quantity sufficient to immerse the solid material,
 b. Subjecting said base vessel, provided with a polytetrafluoroethylene/graphite compound in the form of a stir bar and/or particles, to microwave irradiation, the microwave irradiation being the only heating source and causing at least partial evaporation of the solvent,
 c. Removing said evaporated solvent such that the solvent in the base vessel no longer immerses said support and solid material,
 d. Collecting extracts of the solid material directly from the bottom of the base vessel.

FIGURES

Figure 2:
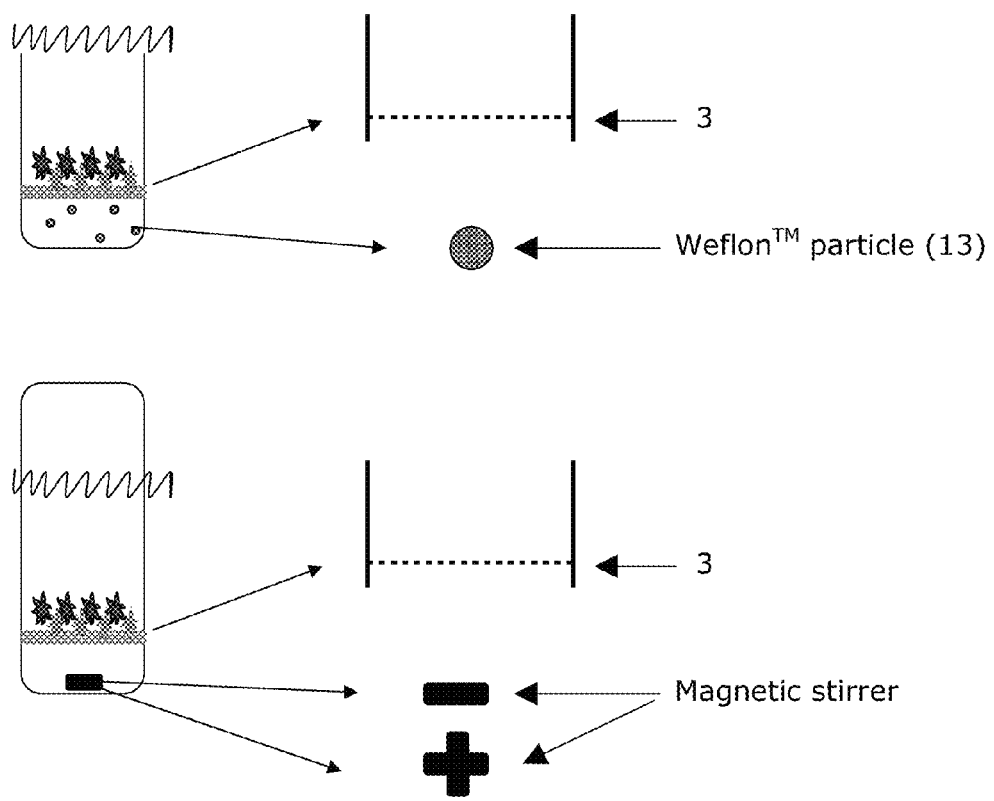
Figure 3:
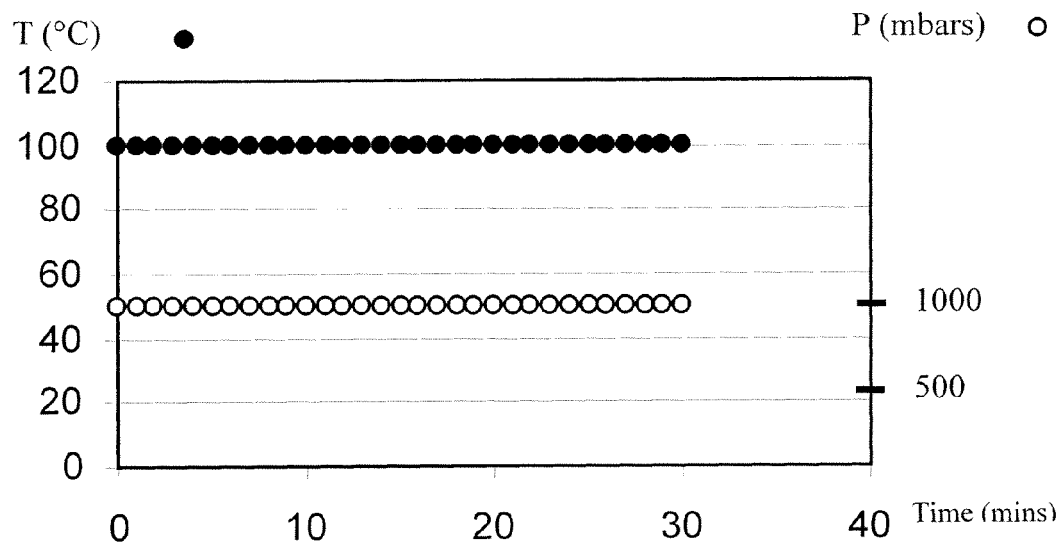
Figure 4:
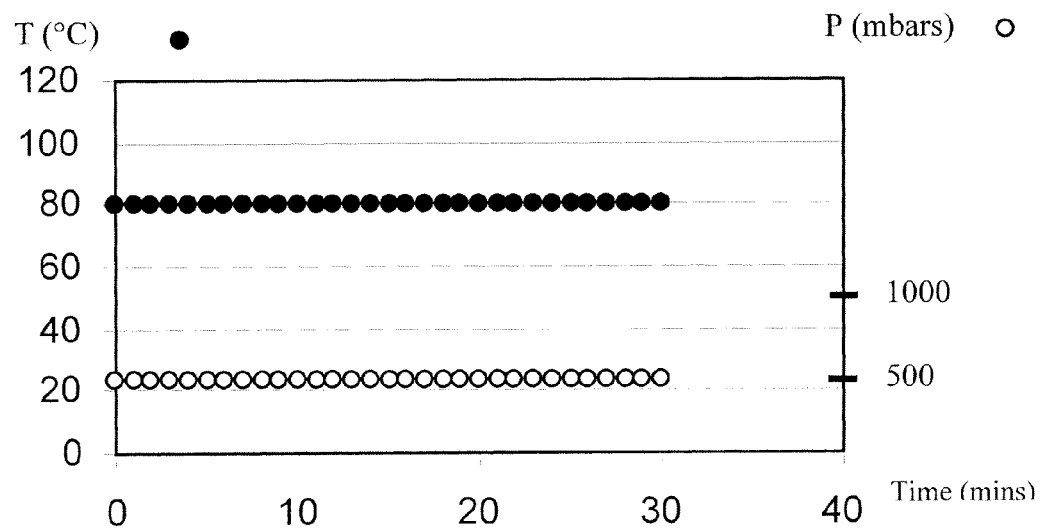
Figure 5:
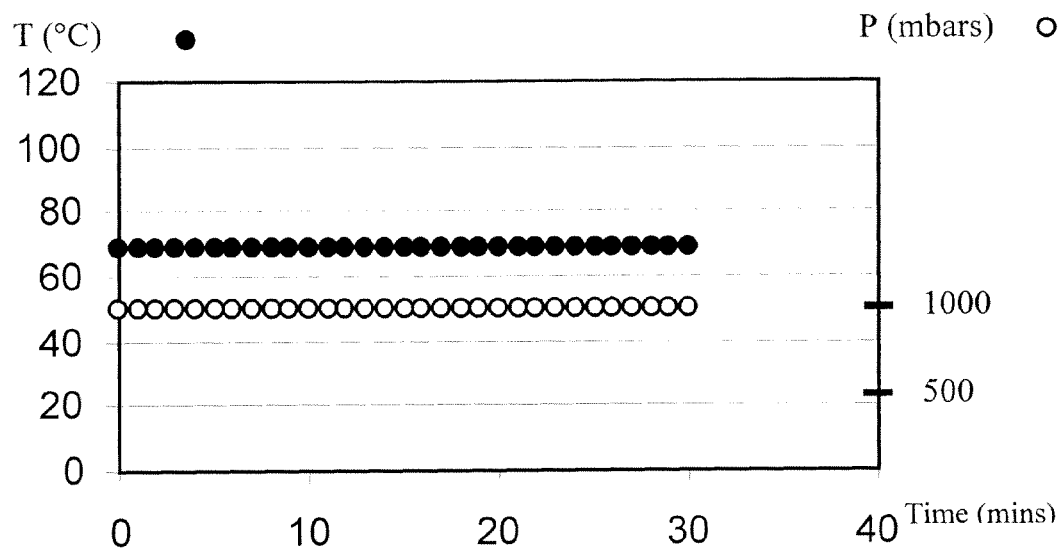
Figure 6:
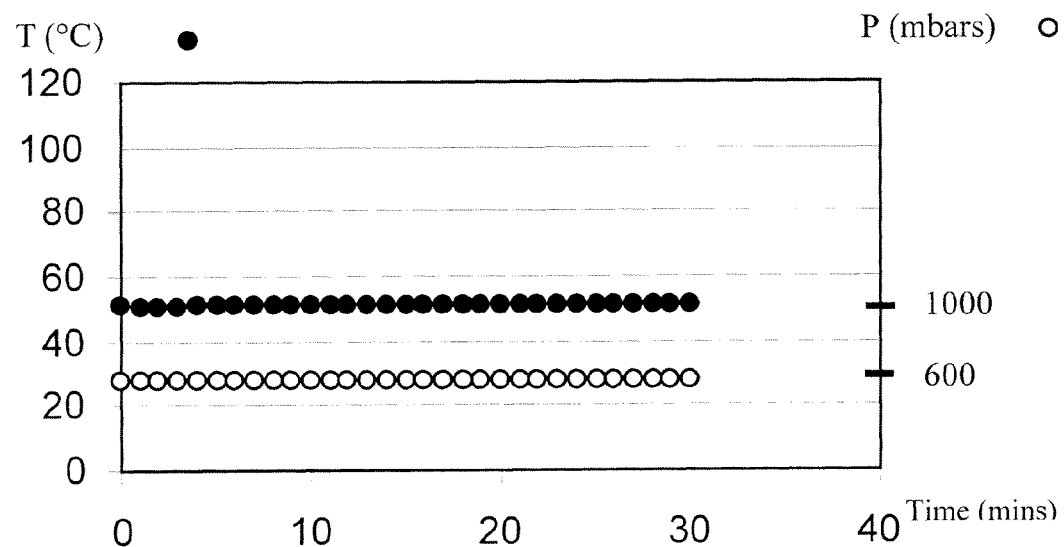

The present invention is further described hereinafter with reference to some of its embodiments shown in the accompanying drawing in which:

FIG. 1 depicts an apparatus suitable for carrying out the method of the invention, FIG. 2 depicts a vessel comprising a support and Weflon™ particles or vessel comprising a magnetic stirrer which may also be made of Weflon™ material, FIG. 3 shows a graph of temperature and pressure versus time for carrying out the method of the invention at atmospheric pressure and with water, FIG. 4 shows a graph of temperature and pressure versus time for carrying out the method of the invention at constant vacuum pressure and with water, FIG. 5 shows a graph of temperature and pressure versus time for carrying out the method of the invention at atmospheric pressure and with n-hexane as solvent, FIG. 6 shows a graph of temperature and pressure versus time for carrying out the method of the invention at constant vacuum pressure and with n-hexane as solvent.

DETAILED DESCRIPTION OF THE INVENTION

Referring to FIG. 1, the device suitable for carrying out the method of the present invention comprises a microwave oven (12) in which a base vessel (1) is placed.

The microwave oven (12) is preferably a multi mode microwave reactor having a twin magnetron (2×800 W, 2455 MHz) with a maximum delivered power of 1000 W variable in 10 W increments. The microwave oven (12) may be any microwave used commonly in the art. For instance, it may be a Milestone ETHOS microwave oven.

The base vessel may be made out of a material which absorbs microwave radiation or, alternatively out of a material which poorly absorbs microwave radiation and does not hinder the propagation of microwaves. Preferably, the base vessel is a traditional glass round-bottom flask. The flask (1) for containing the solid material may be any flask suited for microwave reactions.

The base vessel contains an inner support (3) for placing the solid material (2) to be extracted. Preferably, the inner support covers at least partially the surface area delimited by a horizontal plane of the base vessel. Most preferably, the inner support covers the whole surface area delimited by a horizontal plane of the base vessel.

Typically, the inner support is a porous support. It may be made out of material which absorbs or not microwave radiation. Preferably, the support is made of polytetrafluoroethylene (Teflon®).

The inner support (3) is placed at a defined distance above the bottom of said vessel. This presents the advantage that, after the method has been performed, the solid material (2) placed on said support can easily be separated from the residual solvent which is collected at the bottom of the vessel.

The device for carrying out the present invention further comprises an extraction tube (5) which is placed on top of the base vessel. The extraction tube is typically a glass tube as is commonly used in the art.

Thus, the microwave oven (12) is preferably provided with an opening on its upper surface (11) such that the extraction tube (5) which is fitted on top of the base vessel may extend from inside the microwave oven (12) to outside.

According to a preferred embodiment, a condenser (7) is placed on top of the extraction tube (5) in order to allow the solvent present in the base vessel to reflux upon microwave irradiation. Refluxing allows the sample to be extracted to be repeatedly percolated, thus increasing the extraction yield.

The extraction tube (5) preferably comprises a side arm (6) which is provided with at least one valve and one opening (9). Depending on how the valve is adjusted, the solvent may reflux down the side arm (6) back into the extraction tube (5) and eventually back into the base vessel (1) or when the valve is adjusted accordingly, the refluxing solvent may be collected from the opening (9).

Additionally, the side arm may be provided with another opening (10) which, depending on the application, may be used to pull a vacuum in the system.

The base vessel (1) forming part of the device of the invention, may further contain a compound capable of absorbing microwaves. Such compound is typically a polytetrafluoroethylene/graphite compound. Such material is for example known under the trade name of Weflon™. Said compound may be in the form of a stir bar and/or particles placed at the bottom of the vessel. FIGS. 1 and 2 represent an embodiment where Weflon™ particles (13) are placed in the base vessel. The use of such a compound allows diffusion of heat created by the microwaves to the surroundings and is particularly useful in the case when solvents which are transparent to microwave radiations, i.e. which are not able to absorb microwaves, are used. Using a device shown in FIG. 1, the method of the present invention may be performed as described in the following.

The solid material (2) is first placed inside the base vessel (1) on an inner support (3) which is placed at a defined distance above the bottom of said vessel. Preferably, the support (3) on which the solid material is placed is a polytetrafluoroethylene support. Additionally, it is preferably a porous support.

The solid material may be any material such as food, soil, sediments, pharmaceuticals, plastics, textiles, animal tissues, coal etc. The solid material may also have a moisture content ranging from 0% to 90%.

After placing the solid material (2) in the base vessel (1) on the inner support (3), the solvent is poured into the base vessel up to a level (4a) which immerses the solid material.

The solvent which may be used can be any solvent selected from polar solvents such as water, methanol, ethanol etc. It may also be a non-polar solvent selected from hexane, cyclohexane, limonene etc. Alternatively, the solvent may be a mixture of polar and non-polar solvents. The present method indeed allows any solvent to be used, without the efficiency of the method being compromised.

The base vessel (1) may further contain a polytetrafluoroethylene/graphite compound in the form of a stir bar and/or particles. This is particularly useful in the case when solvents which are weakly polar or non-polar, and which therefore do not absorb microwave radiations, are used.

The base vessel (1) is then sealed and subjected to microwave radiation. The microwave radiation heats, either directly or indirectly, the solvent up to its boiling point and said solvent vapours travel up the extraction tube (5). Thus, the solvent is partially evaporated. The vapours can then be removed from the system by methods known in the art, such that the solvent in the base vessel no longer immerses the support and the solid material (4b). Reducing the level of the solvent in the base vessel thus allows to collect, in a final step, the extracts of the solid material from the bottom of the base vessel.

This new process allows the extraction of solid material in an easy way since a separation step is no longer required and since the extraction and evaporation of the solvent to concentrate the extract is provided in a single step. Furthermore, the setup of the invention is particularly advantageous as it does not require any intervention or modification of the apparatus during the extraction/concentration step.

According to a preferred embodiment of the invention, once the solvent is placed in a base vessel (1) and subjected to microwave radiation, it may be allowed to reflux for a period of time prior to being removed. This is at best carried out by fitting a condenser (7) as shown in FIG. 1 on top of the extraction tube (5). Thus, condensation takes place on the condenser and the condensate drips down onto the sample back into the vessel. If the extraction tube is provided with a side arm (6), the side arm preferably comprises a valve (8) which is adjusted in such a way that the solvent can condense down the side arm and back into the extraction tube (5) and eventually back into the base vessel (1).

After the solvent is allowed to reflux for a period of time, it is removed such that the solid material in the base vessel is no longer immersed in said solvent (4b). Preferably, the solvent is removed via an opening (9) placed on the side arm (6) of the extraction tube (5).

Thereafter, a new batch of solvent can be introduced in the base vessel in order to re-immerse the solid material and allowing the solvent to reflux again for a period of time. After said period of time, the solvent is removed as described above such that the extracts of the solid material are collected at the bottom of the base vessel.

In this preferred embodiment, wherein a new batch of solvent is introduced in the base vessel, an improved extraction is achieved.

The reflux may be carried out for a period of time which can easily be determined by the skilled person. Preferably, the period of time may be between 1 and 100 minutes, more preferably between 3 and 60 minutes, most preferably between 5 and 25 minutes.

This presents a noticeable advantage compared to traditional Soxhlet extraction techniques which normally require between 6 and 24 hours.

The extracts collected at the bottom of the base vessel may be organic compounds such as polycyclic aromatic hydrocarbons, oil, fats, pesticides, dioxins, antioxidants, polyphenols, secondary metabolites, colorants, pigments etc.

The present extraction method may be carried out at constant atmospheric pressure or constant vacuum pressure. When the system is placed under vacuum, such as by pulling a vacuum from the opening (10) on FIG. 1, the boiling point of the solvent is lowered. This is particularly advantageous for thermolabile compounds. For instance, when using water as a solvent the extraction at atmospheric pressure occurs at 100° C. Reducing the pressure to 700 mbars lowers the boiling point of water to 90° C. Further reducing the pressure to 500 mbars will reduce the boiling temperature of water to 80° C. and so on. For instance, the pressure of 150 mbars allows water to boil at 50° C. (cf. FIGS. 3 and 4). Thus, extraction with water can be carried out at a lower temperature than normally possible.

Similarly, when using an organic solvent such as hexane, the temperature of extraction can be reduced from 68.5° C. at atmospheric pressure to about 40° C. at 400 mbars of pressure (cf. FIGS. 5 and 6)

The advantages provided by a method of extraction according to the present invention are numerous. For instance, dried solid material as well as solid material having a high moisture content may be used in the process and be efficiently extracted. The present invention also provides the advantage that any solvent, polar or non polar, may be used which broadens the scope of operation of the present method. Furthermore the present invention also does not require an additional source of heating in that the microwave provides all the heating necessary for carrying out the method. Finally, the extraction time of the present method is not only considerably reduced compared to traditional methods but the process also ensures complete, efficient and accurate extraction of the samples. Using the present method, extraction yields of up to 100% may be obtained.

The present invention is further illustrated by means of non-limiting examples.

EXAMPLES

The process is performed in four steps preceded by the preparation of the material. A Teflon filter support (3) is placed in the base vessel (1).

An amount of 30 g of olive seeds (2) is loaded onto the support (3) and 300 ml of n-hexane is added in order to immerse the sample. Then, the base vessel (1) is placed in the microwave oven (12) and screwed together with the extraction tube (5). The condenser (7) is placed on the extraction tube and the system is started. The irradiation power is fixed at 600 Watts. Then, the condensate drips down onto the sample by adjusting the 3-way valve (8). The extraction is performed for 10 minutes. The level of the solvent is then lowered below the sample by adjusting the 3-way valve (8) accordingly during 2 minutes. Repeated washing of the extraction sample with clean warm solvent follows during 10 minutes with the valve (8) adjusted such that the condensate is directed back into the extraction tube (5).

Finally, the level of the solvent is lowered to concentrate the extract.

The extraction time is 22 minutes versus 8 h of the official method for a percentage of oil extracted of about 51%.

According to the same method, many other solid samples could be extracted such as bakery products, sausage products, fried foods, Cheese, milk, soil, etc.

The invention claimed is:

1. A device suitable for the extraction of solid material by microwave irradiation, said device comprising
   (a) a microwave oven having an upper surface,
   (b) a base vessel having a bottom placed in the microwave oven, said base vessel containing a polytetrafluoroethylene/graphite compound in the form of a stir bar and/or particles and an inner support for placing the solid material to be extracted, said inner support being placed at a defined distance above the bottom of said vessel, and
   (c) an extraction tube placed on top of the base vessel comprising a side arm provided with at least one valve and at least one opening, the microwave oven being provided with an opening on its upper surface such that the extraction tube extends from inside the microwave oven to outside the microwave oven.

2. Device according to claim 1, comprising a condenser fitted on the extraction tube.

3. Device according to claim 1, wherein the valve is adjusted so that the flow of solvent travels through the side arm and back into the extraction tube.

4. Device according to claim 1, wherein the valve is adjusted so that the flow of solvent travels down the side arm and through an opening.

5. Device according to claim 1, wherein the side arm is provided with a further opening.

6. Device according to claim 1, wherein said device is under vacuum.

7. A method for the extraction of solid material, the method comprising the steps of:
   (a) placing the solid material to be extracted and a solvent in a base vessel having a bottom, said solid material being placed on a support placed at a defined distance above the bottom of said vessel,
   said solvent being, when starting the method, in a quantity sufficient to immerse the solid material,
   (b) subjecting said base vessel, provided with a polytetrafluoroethylene/graphite compound in the form of a stir bar and/or particles, to microwave irradiation, the microwave irradiation being the only heating source and causing at least partial evaporation of the solvent into an extraction tube,
   (c) removing said evaporated solvent such that the solvent in the base vessel no longer immerses said support and solid material, and
   (d) collecting extracts of the solid material directly from the bottom of the base vessel.

8. Method according to claim 7, comprising allowing the solvent to reflux for a period of time prior to being removed.

9. Method according to claim 7, comprising, after step (c), the steps of
   (e) introducing a new batch of said solvent in the base vessel in order to re-immerse the support and the solid material placed thereon and allowing the solvent to reflux for a period of time, and
   (f) removing the solvent from the base vessel such that the extracts of said solid material are collected at the bottom of the base vessel.

10. Method according to claim 8, wherein the period of time of reflux is between 1 minute and 100 minutes.

11. Method according to claim 7, wherein the solid material is selected from the group consisting of food, soil, sediments, pharmaceuticals, plastics, textiles, animal tissues, and coal.

12. Method according to claim 7, wherein the solid material has a moisture content of 0-90%.

13. Method according to claim 7, wherein the extracts are organic compounds selected from the group consisting of polycyclic aromatic hydrocarbons (PAHs), oils, fats, pesticides, dioxins, antioxidants, polyphenols, secondary metabolites, colorants, and pigments.

14. Method according to claim 7, wherein the solvent is a polar solvent.

15. Method according to claim 7, wherein the support is a polytetrafluoroethylene support.

16. Method according to claim 7, wherein the support is a porous support.

17. Method according to claim 7, comprising removing solvent by adjusting a valve placed on a side arm of an extraction tube such that the solvent is collected from an opening on said side arm, said extraction tube being placed directly above the base vessel.

18. Method according to claim 7, comprising carrying out said method at constant vacuum pressure or at atmospheric pressure.

19. Method according to claim 17, comprising pulling a vacuum from an opening on the side arm of the extraction tube.

20. Method according to claim 8, wherein the period of time of reflux is between 3 minutes and 60 minutes.

21. Method according to claim 8, wherein the period of time of reflux is between 5 minutes and 25 minutes.

22. Method according to claim 7, wherein the solvent is a non-polar solvent.

23. Method according to claim 7, wherein the solvent is a mixture of at least one polar solvent and at least one non-polar solvent.

24. Method according to claim 18, comprising pulling a vacuum from an opening on the side arm of the extraction tube.

25. Method according to claim 22, wherein the non-polar solvent is selected from the group consisting of hexane, cyclohexane, and limonene.

* * * * *